(12) United States Patent
Yoshimoto et al.

(10) Patent No.: US 10,647,978 B2
(45) Date of Patent: May 12, 2020

(54) SOLUTION FOR EXTRACTION OF RNA

(71) Applicant: Toray Industries, Inc., Tokyo (JP)

(72) Inventors: Makiko Yoshimoto, Kamakura (JP);
Hideo Akiyama, Kamakura (JP);
Hitoshi Nobumasa, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 236 days.

(21) Appl. No.: 15/581,344

(22) Filed: Apr. 28, 2017

(65) Prior Publication Data

US 2017/0247681 A1 Aug. 31, 2017

Related U.S. Application Data (63) Continuation of application No. 13/816,792, filed as application No. PCT/JP2011/068620 on Aug. 17, 2011, now abandoned.

(30) Foreign Application Priority Data

Aug. 18, 2010 (JP) .................................. 2010-183280

(51) Int. Cl.
C12Q 1/68 (2018.01)
C12N 15/10 (2006.01)
G01N 1/28 (2006.01)
C07H 21/04 (2006.01)

(52) U.S. Cl.
CPC ......... C12N 15/1003 (2013.01); G01N 1/286 (2013.01); *G01N 2001/2866* (2013.01)

(58) Field of Classification Search
None
See application file for complete search history.

(56) References Cited

U.S. PATENT DOCUMENTS

| 4,843,155 | A | | 6/1989 | Chomczynski | |
| 5,346,994 | A | * | 9/1994 | Chomczynski | C07K 1/14 530/419 |
| 7,749,519 | B2 | * | 7/2010 | Sim | C07K 14/445 424/184.1 |
| 2003/0204077 | A1 | | 10/2003 | Simms | |
| 2011/0195030 | A1 | | 8/2011 | Mumper et al. | |

FOREIGN PATENT DOCUMENTS

| EP | 0554034 A1 | 8/1993 |
| GB | 190600753 | 12/1906 |
| JP | 5344886 A | 12/1993 |
| JP | 2007532140 A | 11/2007 |
| WO | 9528409 A1 | 10/1995 |
| WO | 9845311 A1 | 10/1998 |
| WO | 2005103252 A1 | 11/2005 |
| WO | 2008157316 A1 | 12/2008 |

OTHER PUBLICATIONS

Supplemental European Search Report dated Dec. 17, 2013, A0pplication No. EP 11818210.
Chomczynski P. et al., "Single-step Method of RNA Isolation by Acid Guanidinium Thiocyanate-Phenol-Chloroform Extraction", Analytical Biochemistry, Academic Press Inc., New York, vol. 162, No. 1, Apr. 1987, pp. 156-159.
International Search Report dated Nov. 15, 2011, Application No. PCT/JP2011/068620, 1 page.
Final Office Action for U.S. Appl. No. 13/816,792, dated Apr. 7, 2016, 18 pages.
Non Final Office Action for U.S. Appl. No. 13/816,792, dated Jun. 5, 2015, 13 pages.
Final Office Action for U.S. Appl. No. 13/816,792, dated Dec. 3, 2014, 20 pages.
Non Final Office Action for U.S. Appl. No. 13/816,792, dated May 2, 2013, 16 pages.
Entire Prosecution History for U.S. Appl. No. 13/816,792, filed Feb. 13, 2013, entitled "Solution for Extraction of RNA".
Non Final Office Action for U.S. Appl. No. 16/048,695, dated Oct. 8, 2019, 19 pages.

\* cited by examiner

*Primary Examiner* — Bradley L. Sisson
(74) *Attorney, Agent, or Firm* — RatnerPrestia (57) ABSTRACT

A solution for extracting substantially pure RNA from a biological sample is disclosed. The solution for extracting RNA from a biological sample containing RNA and at least DNA comprises:
(a) phenol in an amount of more than 50% by volume based on the total amount of the solution;
(b) a polyol in an amount of 3 to 10% by volume based on the total amount of the solution;
(c) a guanidinium salt at a concentration of 0.5 to 2.0 M based on the total amount of the solution;
(d) a thiocyanate at a concentration of 0.1 to 0.5 M based on the total amount of the solution; and
(e) a buffer for maintaining the pH of the solution at 4 to 6.

9 Claims, 5 Drawing Sheets

SOLUTION FOR EXTRACTION OF RNA

CROSS REFERENCE TO RELATED APPLICATIONS

This Application is a Continuation Application of U.S. application Ser. No. 13/816,792, filed Feb. 13, 2013 which claims priority to U.S. National Phase application of PCT International Application No. PCT/JP2011/068620, filed Aug. 17, 2011, and claims priority to Japanese Patent Application No. 2010-183280, filed Aug. 18, 2010, the disclosures of these applications are incorporated herein by reference in their entireties for all purposes.

FIELD OF THE INVENTION

The present invention relates to a solution for extracting substantially pure RNA from a biological sample.

BACKGROUND OF THE INVENTION

Genetic information written in DNA is transcribed into RNA in various combinations, to produce complicated phenotypes of organisms. Contribution of RNA to phenotypes of organisms is known to be dependent on the types and expression levels of the RNA, and extraction of highly pure RNA from various biological materials is important for performing gene expression analysis. For achievement of this object, many methods for extraction of RNA have been developed so far. Examples of methods for isolation of RNA frequently employed include phenol extraction, precipitation from chaotropic salt solutions and adsorption to silica membranes.

Patent Document 1 discloses a solution for RNA extraction comprising 2 to 5 M guanidine and 40 to 60% phenol. RNA extraction had required not less than 2 days of operation using an ultracentrifuge before, but use of this solution enabled efficient extraction of RNA in 3 hours. This method is called the single-step method.

By improvement of the method described in the above Patent Document 1, Patent Document 2 discloses an extraction solution for simultaneous extraction and separation of RNA, DNA and proteins from a sample comprising of these components. More specifically, the literature describes extraction and separation of RNA into an aqueous layer by using a 30 to 50% phenol solution containing 0.5 to 2 M guanidine.

Although the solutions described in Patent Documents 1 and 2 have different compositions, RNA can be extracted by similar operations using the solutions. That is, each solution is used for homogenization of a biological tissue, and a hydrophobic organic solvent such as chloroform is used upon centrifugation of the homogenate to achieve layer separation. Thereafter, the aqueous layer in the uppermost part comprising RNA is recovered. RNA is then precipitated with alcohol and washed in order to extract RNA.

However, RNA isolated using the solutions and the methods described in Patent Document 1 and 2 still shows contamination with (residual) genomic DNA in an amount which can be detected by the reverse transcription-polymerase chain reaction assay (RT-PCR), leading to problems such as loss of quantitativeness of RNA in cases of RT-PCR (Patent Document 3, e.g., paragraph 0005). Therefore, RNA isolated by these methods needs to be further purified for removal of DNA as a contaminant.

A commonly used method for removal of DNA contained as an impurity in an extracted RNA sample is treatment of the RNA sample with deoxyribonuclease (DNase). However, in cases where treatment with DNase is carried out in a liquid layer, it is necessary to perform phenol/chloroform extraction and denaturation of proteins again for removal of DNase after the treatment. Further, in cases where the extraction is performed using a combination of silica membrane columns, the operation of washing the columns needs to be carried out repeatedly. Although contamination with DNA is reduced by this treatment with DNase, such additional labor is required and loss of RNA occurs, resulting in a decreased amount of extracted RNA, which is problematic.

As a method for avoiding contamination of an RNA sample with DNA without performing DNase treatment, Patent Document 3 reports a method using an RNA extraction reagent at a pH of less than 4. However, it is well known that nucleic acid is depurinated and degraded under acidic conditions, and it is therefore difficult to isolate substantially intact RNA. Further, since the solution equilibrium of DNA into the aqueous/organic layer under acidic conditions is biased toward distribution into the organic layer, the effect of suppressing contamination of the aqueous phase with genomic DNA can be expected to some extent by using a reagent for extraction of RNA at a pH of less than 4, but complete suppression of contamination with small DNA fragments having small numbers of bases is impossible.

PATENT DOCUMENTS

Patent Document 1: U.S. Pat. No. 4,843,155 B
Patent Document 2: JP 5-344886 A
Patent Document 3: Japanese Translated PCT Patent Application Laid-open No. 2007-532140

SUMMARY OF THE INVENTION

As described above, substantially pure RNA free from contamination with DNA cannot be extracted with conventional solutions for extraction of RNA from biological samples even in cases where quantitativeness is required, which has been problematic. Therefore, for removal of DNA as a contaminant, an additional step such as DNase treatment has been necessary. The present invention aims to solve these problems and provides a solution for extracting substantially pure RNA from a biological sample.

The present inventors studied compositions of conventional solutions for RNA extraction and discovered that the phenol concentration has an especially strong relationship with the effect of prevention of contamination with DNA, thereby completing the present invention.

That is, the present invention provides the following:

[1] A solution for extracting RNA from a biological sample containing RNA and at least DNA, the solution comprising:
  (a) phenol in an amount of more than 50% by volume based on the total amount of the solution;
  (b) a polyol in an amount of 3 to 10% by volume based on the total amount of the solution;
  (c) a guanidinium salt at a concentration of 0.5 to 2.0 M based on the total amount of the solution;
  (d) a thiocyanate at a concentration of 0.1 to 0.5 M based on the total amount of the solution; and
  (e) a buffer for maintaining the pH of the solution at 4 to 6.

[2] The solution according to [1], wherein the phenol concentration is 55 to 65% by volume based on the total amount of the solution.

[3] The solution according to [1] or [2], further comprising an organic solvent for separating an aqueous layer.

[4] The solution according to any one of [1] to [3], wherein the biological sample is a culture liquid of cultured cells.
[5] The solution according to any one of [1] to [3], wherein the biological sample is a body fluid component of an organism.
[6] The solution according to any one of [1] to [3], wherein the biological sample is a blood component of an organism
[7] A method for extracting RNA from a biological sample containing RNA and at least DNA, the method comprising the steps of:
  homogenizing the biological sample together with a solution comprising:
    (a) phenol in an amount of more than 50% by volume based on the total amount of the solution;
    (b) a polyol in an amount of 3 to 10% by volume based on the total amount of the solution;
    (c) a guanidinium salt at a concentration of 0.5 to 2.0 M based on the total amount of the solution;
    (d) a thiocyanate at a concentration of 0.1 to 0.5 M based on the total amount of the solution; and
    (e) a buffer for maintaining the pH of the solution at 4 to 6;
  mixing the obtained homogenate with an organic solvent for separation of an aqueous layer;
  centrifuging the obtained mixture; and
  recovering an RNA-containing aqueous layer produced by the centrifugation.
[8] A method for extracting RNA from a biological sample containing RNA and at least DNA, the method comprising the steps of:
  homogenizing the biological sample together with a solution comprising:
    (a) phenol in an amount of more than 50% by volume based on the total amount of the solution;
    (b) a polyol in an amount of 3 to 10% by volume based on the total amount of the solution;
    (c) a guanidinium salt at a concentration of 0.5 to 2.0 M based on the total amount of the solution;
    (d) a thiocyanate at a concentration of 0.1 to 0.5 M based on the total amount of the solution;
    (e) a buffer for maintaining the pH of the solution at 4 to 6; and
    (f) an organic solvent for separation of an aqueous layer;
  centrifuging the obtained homogenate; and
  recovering an RNA-containing aqueous layer produced by the centrifugation.
[9] The method according to claim 7 or 8, wherein the phenol concentration is 55 to 65% by volume based on the total amount of the solution of (a) to (e).

By using the solution of the present invention, substantially pure RNA free from contamination with DNA can be simply extracted from a biological sample. Further, by the present invention, RNA can be obtained without an additional treatment such as DNase treatment which may cause recovery loss, which RNA has purity that allows use of the RNA as it is even in uses wherein quantitativeness is required. In particular, an RNA of interest can be extracted with high purity even from, among biological samples, body fluids such as blood containing very large amounts of RNase and other contaminants.

DETAILED DESCRIPTION OF EMBODIMENTS OF THE INVENTION

The present invention provides a solution for extracting RNA from a biological sample, which solution comprises as its components the following (a) to (e):
  (a) phenol in an amount of more than 50% by volume based on the total amount of the solution;
  (b) a polyol in an amount of 3 to 10% by volume (not less than 3% by volume and not more than 10% by volume) based on the total amount of the solution;
  (c) a guanidinium salt at a concentration of 0.5 to 2.0 M (not less than 0.5 M and not more than 2.0 M) based on the total amount of the solution;
  (d) a thiocyanate at a concentration of 0.1 to 0.5 M (not less than 0.1 M and not more than 0.5 M) based on the total amount of the solution; and
  (e) a buffer for maintaining the pH of the solution at 4 to 6.

The biological sample used in the present invention comprises RNA and at least DNA. Further, by using the solution of the present invention, substantially pure RNA can be extracted from the biological sample. The term "substantially pure RNA" herein means RNA from which DNA contained in the original biological sample has been separated and which is substantially free from contamination with the DNA. Whether or not RNA is substantially pure can be judged by seeing whether or not DNA is detected by electrophoresis. For example, since "Agilent RNA 6000 pico kit" manufactured by Agilent Technologies Inc. (model number, 5067-1513) can be used for detection of nucleic acid in an amount of 50 pg/μL to 5000 pg/μL (recommendation), the kit can be used for evaluation of the presence/absence of DNA contamination. More specifically, the extracted nucleic acid may be treated with RNase and subjected to electrophoresis using "Agilent RNA 6000 pico kit". In cases where no peak was detected, it can be said that DNA contamination was sufficiently suppressed and substantially pure RNA could be obtained. Further, by analyzing the amount of DNA contamination by quantitative PCR, the purity of RNA can be evaluated. For example, in cases where a real-time PCR apparatus and "SYBR Green" (fluorescent dye) are used, double-stranded DNA in an amount of 60 pg can be detected, so that the evaluation can be carried out using these. More specifically, extracted nucleic acid is added to a PCR reaction solution containing primers, DNA polymerase and "SYBR Green" to perform PCR amplification, and the result is compared with a preliminarily prepared calibration curve. By this, the amount of DNA contamination can be quantitatively analyzed.

In the present invention, the total amount of a solution means the total volume comprising all of the above-described (a) to (e). For example, "phenol in an amount of more than 50% by volume based on the total amount of the solution" means that more than 500 mL of phenol is contained in 1 L of the solution after mixing of all components. Further, for example, "a guanidinium salt at a concentration of 0.5 to 2.0 M based on the total amount of the solution" means that the final concentration in the solution is not less than 0.5 M and not more than 2.0 M, that is, the guanidinium salt is contained in an amount of not less than 0.5 mol and not more than 2 mol in 1 L of the solution after mixing of all components.

The solution according to an embodiment of the present invention comprises (a) phenol in an amount of more than 50% by volume based on the total amount of the solution. It was found that employing a phenol concentration of more than 50% by volume, which is different from the concentration employed in conventional techniques, produces the effect of reducing contamination of the aqueous layer, into which RNA is extracted, with DNA as an impurity. For example, the solution according to an embodiment of the present invention comprises phenol in an amount of not less than 51% by volume, not less than 52% by volume, not less than 53% by volume, not less than 54% by volume or not less than 55% by volume. The solution of the present invention comprises phenol in an amount of preferably not less than 53% by volume, more preferably not less than 55% by volume. Further, the concentration of phenol is preferably not more than 75% by volume in view of preparing the solution of the present invention in the state where other components of the solution of the present invention, (b) polyalcohol, (c) 0.5 to 2.0 M guanidinium salt and (d) 0.1 to 0.5 M thiocyanate are uniformly mixed at the respective predetermined concentrations. Further, the concentration of phenol is more preferably not more than 65% by volume in view of reducing the influence of oxidation of phenol. The range of the phenol concentration is preferably one determined by an arbitrary combination of these upper limits and lower limits, and is more preferably not less than 52% by volume and not more than 65% by volume, not less than 53% by volume and not more than 65% by volume, especially preferably not less than 55% by volume and not more than 65% by volume.

The solution according to an embodiment of the present invention comprises (b) a polyol in an amount of 3 to 10% by volume based on the total amount of the solution. The polyol in the present invention may be an aliphatic alcohol having a plurality of hydroxyl groups, which allows mixing of the (a) phenol component and the aqueous solutions of (c) and (d) in the solution of the present invention, to keep the solution of the present invention uniform. As the polyol, a $C_2$-$C_6$ aliphatic alcohol having 2 to 4 hydroxyl groups is preferred. Examples of the polyol include glycerol, ethylene glycol, propylene glycol and erythritol, and the polyol is more preferably glycerol. The polyol may be used in an amount of 3 to 10% by volume based on the total amount of the solution of the present invention in order to maintain the solution of the present invention as a uniform solution and to prevent excessive distribution of the phenol component into the aqueous layer.

The solution according to an embodiment of the present invention comprises (c) a guanidinium salt at a concentration of 0.5 to 2.0 M based on the total amount of the solution. Specific preferred examples of the guanidinium salt include guanidinium thiocyanate and guanidinium hydrochloride. Guanidinium salts have an effect to protect RNA from degradation and to keep phenol in the solution state in an aqueous solution.

The solution according to an embodiment of the present invention comprises (d) a thiocyanate at a concentration of 0.1 to 0.5 M based on the total amount of the solution. As the thiocyanate, an inorganic salt of thiocyanic acid may be preferably used, and ammonium thiocyanate and sodium thiocyanate may be more preferably used. Further, the thiocyanate may be a mixture of a plurality of different inorganic salts of thiocyanic acid, and, for example, a mixture of ammonium thiocyanate and sodium thiocyanate may be preferably used. Thiocyanate is considered to enhance RNA extraction from a biological sample. In cases where the solution of the present invention comprises guanidinium thiocyanate, the concentration of guanidinium thiocyanate is included in the concentration of the above-described guanidinium salt, and not included in the concentration of thiocyanate.

The solution according to an embodiment of the present invention comprises (e) a buffer for maintaining the pH of the solution at 4 to 6. As the buffer, organic salts and inorganic salts which are conventionally used for maintaining the pH within a desired range and show buffering capacity may be used. Specific examples of the buffer include organic salts and inorganic salts, such as phosphate, acetate, citrate, phthalate, tartrate and lactate, of sodium, potassium, lithium and ammonium. Among the combinations of these, sodium acetate and sodium citrate are more preferably used. Further, a plurality of these organic salts and/or inorganic salts may be used in combination. The concentration of the buffer is not restricted as long as it is sufficient for maintaining the pH within the desired range of 4 to 6, and the concentration is preferably 0.02 to 0.2 M based on the total amount of the solution of the present invention. In order to adjust the pH of the solution of the present invention, an appropriate aqueous acid or alkaline solution such as a hydrochloric acid or sodium hydroxide solution may be added as appropriate in addition to the buffer.

The solution of the present invention may contain a surfactant(s) such as polyoxyethylene sorbitan, sodium dodecyl sulfate and/or sarcosine for supporting purification of the RNA of interest by denaturing proteins in the biological sample. Further, the solution of the present invention may contain an antioxidant(s) such as hindered amine phenol and/or quinoline for prevention of oxidation of phenol.

In cases where the biological sample is in the liquid state when the RNA of interest is to be extracted, the solution of the present invention may be used in an amount of not less than 1 volume, preferably not less than 3 volumes of the sample.

An example of the procedure for extraction of the RNA of interest using the solution of the present invention is shown below. First, the biological sample is homogenized in the solution of the present invention to form a homogenate. The method of homogenization is not restricted, and examples of the method include stirring by vortexing or the like, crushing with an injection needle or the like, and use of a conventional homogenizer. Subsequently, an organic solvent is added to the homogenate for separation of the aqueous layer, and the resulting mixture is subjected to centrifugation. The organic solvent to be added in this step is preferably used in an amount of about 2% by volume to about 40% by volume based on the homogenate. The centrifugation may be carried out usually at 6,000×G to 20,000×G for 3 minutes to 30 minutes, for example, at a rate of 12,000×G for 10 minutes at room temperature. However, the rate, temperature and time are not restricted as long as the aqueous layer can be separated. By the centrifugation, the substantially pure RNA of interest is extracted into the aqueous layer. On the other hand, DNA, proteins and the like are separated into the organic layer, or, in cases where an intermediate layer was produced, DNA, proteins and the like are separated into the organic layer and the intermediate layer.

The organic solvent for separation of the aqueous layer is a liquid organic compound to be used for achieving separation into the aqueous layer comprising the RNA of interest extracted using the solution of the present invention and the organic layer and/or the intermediate layer (if produced) comprising DNA and the like. As this organic solvent, one which has the same degree of hydrophilicity as, or is more hydrophobic than, phenol may be used. For example, in terms of the water/octanol distribution coefficient C Log P which is commonly used as an index of hydrophilicity, an organic compound having a value of not less than 1.4 (C Log P value for phenol) may be used, and an organic compound having a value within the range of 1.4 to 5 may be preferably used. An estimated value of the C Log P value can be calculated by, for example, using a program such as "Chem Draw" (registered trademark). Examples of the organic solvent which may be used in the present invention include, but are not limited to, chloroform (1.952), p-bromoanisole (3.064), 1-bromo-3-chloropropane (1.847), 4-bromoveratrole (2.7345), 6-bromo-1,4-benzodioxane (3.0005), 1-bromo-4-trifluoromethoxybenzene (4.173), 1-bromo-2,4-dimethoxybenzene (2.8545), 4-fluoroanisole (2.344), 4-bromotoluene (3.504) and ethyl 4-bromobutyrate (1.772). The value in the parentheses for each of the above organic solvents indicates the C Log P value calculated with "Chem Draw".

The organic solvent for separation of the aqueous layer may be used by formation using the solution of the present invention comprising (a) to (e) as described above and addition to the homogenate, but the organic solvent may also be preliminarily contained in the solution of the present invention comprising the above-described (a) to (e). In cases of a conventional solution whose phenol concentration is not more than 50%, inclusion of this organic solvent in advance causes separation of the solution into the aqueous layer and the organic layer before mixing with a biological sample, so that it has been difficult to use the solution as an extraction solution. In contrast, at the phenol concentration of the solution of the present invention, the organic solvent can be uniformly mixed with the solution of the present invention, and the resulting solution can be stored as a single solution. In cases of the solution of the present invention preliminarily containing the organic solvent, separation of the aqueous phase containing RNA is possible by adding a biological sample to the solution and homogenizing the resulting mixture to provide a homogenate, followed by immediately subjecting the homogenate to centrifugation. Accordingly, compared to the cases where addition of the organic solvent to the homogenate is carried out later, the procedure can be made very simple, which is preferred.

In cases where the organic solvent for separation of the aqueous layer is preliminarily contained in the solution of the present invention comprising the above-described (a) to (e), the content of the organic solvent may be selected depending on the type of the organic solvent to be added and the phenol concentration in the solution, within the range in which the organic solvent can be uniformly mixed in the solution of the present invention. For example, in cases where the phenol concentration in the solution of the present invention is 65% and chloroform is selected as the organic solvent, chloroform is contained preferably in an arbitrary volume of up to 27% by volume based on the total amount, 100%, of the solution comprising the above-described (a) to (e). More specifically, it is preferred to add chloroform in an arbitrary volume of up to 27 mL, to 100 mL of the solution comprising the above-described (a) to (e). Chloroform is contained in an amount of more preferably 5 to 25% by volume, still more preferably 10 to 20% by volume based on the total amount, 100%, of the solution comprising the above-described (a) to (e). Further, in cases where the phenol concentration is 58%, chloroform is contained preferably in an arbitrary volume of up to 14%, more preferably in an amount of 6 to 13% by volume, still more preferably in an amount of 8 to 12% by volume based on the total amount, 100%, of the solution comprising the above-described (a) to (e). Further, in cases where the phenol concentration in the solution is 65% and p-bromoanisole is selected as the organic solvent, p-bromoanisole is contained preferably in an arbitrary volume of up to 22% by volume, more preferably in an amount of 5 to 20% by volume, still more preferably in an amount of 10 to 18% by volume based on the total amount, 100%, of the solution comprising the above-described (a) to (e). Further, similarly, in cases where the phenol concentration is 58%, p-bromoanisole is contained preferably in an arbitrary volume of up to 13% by volume, more preferably in an amount of 3 to 11% by volume, still more preferably in an amount of 5 to 9% by volume based on the total amount, 100%, of the solution comprising the above-described (a) to (e).

For further purifying and concentrating the RNA extracted into the aqueous layer using the solution of the present invention, a lower alcohol may be added to the aqueous layer comprising RNA in order to precipitate the RNA, and the precipitated RNA may be recovered. Alternatively, the RNA precipitated by addition of a lower alcohol to the aqueous layer comprising RNA may be adsorbed to a carrier to which RNA can be adsorbed, such as a silica membrane column, and the RNA may then be eluted and recovered from the carrier (column). Examples of the lower alcohol to be used in this step include ethanol and isopropanol. The concentration of the lower alcohol may be determined according to those employed in conventional techniques such as ethanol precipitation and isopropanol precipitation, or according to the concentrations recommended by manufacturers of carriers such as silica membrane columns.

The solution of the present invention can be produced by mixing the above-described (a) to (e) such that their respective concentrations are attained. The procedure of the mixing is not restricted. Depending on the composition of the solution, the respective solutions at higher concentrations may be prepared in advance before mixing the solutions. For example, 6 M aqueous guanidinium thiocyanate solution, 6 M aqueous ammonium thiocyanate solution and 1 M sodium acetate may be prepared in advance and then mixed to attain the concentrations of interest, followed by addition of glycerol, phenol and a necessary amount of water thereto, to prepare the solution of the present invention. The solution of the present invention wherein an organic solvent for separation of the aqueous layer is preliminarily contained in the solution comprising the above-described (a) to (e) can also be similarly produced by mixing (a) to (e) and the organic solvent such that their desired concentrations are attained.

The biological sample to be used in the present invention is not restricted as long as it comprises RNA and at least DNA. For example, the biological sample may comprise, in addition to DNA, proteins as impurity components which are preferably separated from the RNA of interest. Specific examples of the biological sample include cultured cells; culture liquids of cultured cells; body tissues such as surgical sections and biopsy samples; living cells; blood; blood components (serum, plasma); urine; and body fluids such as saliva and tears. The biological sample is not restricted to these, and an arbitrary sample containing RNA may be used. When the solution of the present invention is applied to these biological samples, in cases where the biological sample is a liquid sample such as a body fluid, the collected sample may be mixed as it is with the solution of the present invention or may be diluted with PBS or water before mixing with the solution of the present invention. In cases where the biological sample is a cell pellet or a tissue piece, the collected sample may be mixed as it is with the solution of the present invention or may be diluted with PBS or water before mixing with the solution of the present invention, and, in cases where the sample is diluted, a homogenate of the biological sample is preferably prepared before dilution with water or PBS in order to prevent degradation of RNA.

Among the biological samples, body fluids, especially blood, sometimes contain a very large amount of RNase and other contaminants, and, in such a case, extraction of substantially pure RNA by a conventional method is very difficult. With a phenol concentration of more than 50% by volume, the solution of the present invention enables effective extraction of contaminants such as proteins into an organic layer, so that the RNA of interest can be obtained with high purity. Further, the intermediate layer that appears after centrifugation is reduced and clear separation into layers can be achieved, so that the aqueous layer comprising the RNA of interest can be easily separated.

The RNA extracted using the solution is ribonucleic acid wherein a plurality of ribonucleotides are linked by phosphodiester bonds, and the molecular weight, the number of bases and the origin of the RNA are not restricted. In general, RNA is classified into many types according to functional classification, and examples of the types include mRNA (messenger RNA), tRNA (transfer RNA), rRNA (ribosomal RNA), ncRNA (non-coding RNA), snRNA (small nuclear RNA) and snoRNA (small nucleolar RNA). However, in view of the chemical structure, the only known difference is the molecular weight (number of bases), and RNA having any molecular weight is included in the present invention. RNAs having base numbers of about 15 to 500 bases, which are generally called small RNAs, and RNAs generally having base numbers of about 18 to 25, which are miRNAs (microRNAs), are also included in the RNA of the present invention.

In general, the main difference in the primary chemical structure between RNA and DNA is the presence/absence of the hydroxyl group (—OH) at the 2'-position of ribose as the constituent sugar. The smaller the number of bases, the smaller the structural difference between RNA and DNA and the more difficult separation of RNA and DNA by extraction. However, by use of the solution of the present invention, RNA having a relatively small number of bases such as small RNA can also be extracted with high purity.

In the state where DNA and RNA coexist, it is usually difficult to distinguish between these and to quantify each of these using an absorptiometer or luminometer. However, by using the solution of the present invention, substantially pure RNA can be obtained, so that quantification of RNA using an absorptiometer or luminometer is possible. Further, in cases where the solution of the present invention is used in RNA analysis using qRT-PCR or a microarray, the analysis can be simply carried out without requirement of treatment with DNase, in the absence of the noise due to coexistence of DNA.

EXAMPLES

The present invention will now be described concretely by way of Examples below. However, the scope of the present invention is not restricted by these Examples.

Example 1

(1) Preparation of Solution for RNA Extraction

The respective components of the solution were mixed such that their final concentrations were as described below, to prepare a solution for RNA extraction.
58 vol % Phenol
5 vol % Glycerol
0.8 M Guanidinium thiocyanate (mixed as an aqueous solution)
0.4 M Ammonium thiocyanate (mixed as an aqueous solution)
0.1 M Sodium acetate buffer (mixed as an aqueous solution), adjusted to pH 5.

(2) RNA Extraction from Biological Sample

As a biological sample containing RNA as well as DNA and proteins, serum was used for RNA extraction. By mixing 900 µL of the solution prepared in the above (1) and 300 µL of serum by vortexing, the sample was homogenized. To the resulting homogenate, 60 µL of p-bromoanisole was added, and the resulting mixture was mixed, followed by centrifuging the mixture at room temperature at 12,000×G for 10 minutes. By this, an aqueous layer containing RNA, and an organic layer and an intermediate layer containing DNA and proteins were formed. From these, 400 µL of the aqueous layer was separated into another tube.

(3a) Purification and Concentration of RNA from Aqueous Layer—without Enzyme Treatment—

To the aqueous layer containing RNA separated in (2), 1.5 volumes of 100% ethanol was added, and 700 µL of the resulting mixture was placed in a column for purification of nucleic acid, "RNeasy Mini Spin Column" contained in "miRNeasy mini kit" (manufactured by QIAGEN), followed by centrifuging the column at 8,000×G for 15 seconds to allow adsorption of nucleic acid to the column. The liquid that passed through the column was discarded. By repeating this operation until no ethanol-mixed RNA sample is remaining, all nucleic acid contained in the aqueous layer was adsorbed to the column. Thereafter, according to the protocol for "miRNeasy mini kit", the column was washed twice with 700 µL of Buffer RWT and 500 µL of Buffer RPE, and the column was then dried, followed by elution with 30 µL of RNase-free water, to obtain a purified and concentrated RNA sample.

(3b) Purification and Concentration of RNA from Aqueous Layer—with RNase Treatment—

In order to confirm that the extracted nucleic acid is RNA, the sample separated in (2) was subjected to RNase treatment. To the aqueous layer containing RNA separated in (2), 1.5 volumes of 100% ethanol was added, and nucleic acid was allowed to adsorb to the column in the same manner as in (3a). After washing the column with 350 µL of Buffer RWT, diluted RNase was added thereto to perform RNase treatment of the nucleic acid adsorbed to the column, and the column was washed twice with 350 µL of Buffer RWT and 500 µL of Buffer RPE, followed by drying the column. Thereafter, elution was carried out with 30 µL of RNase-free water, to obtain a purified and concentrated RNA sample.

(4) Evaluation of Purity by Electrophoresis

Figure 1:
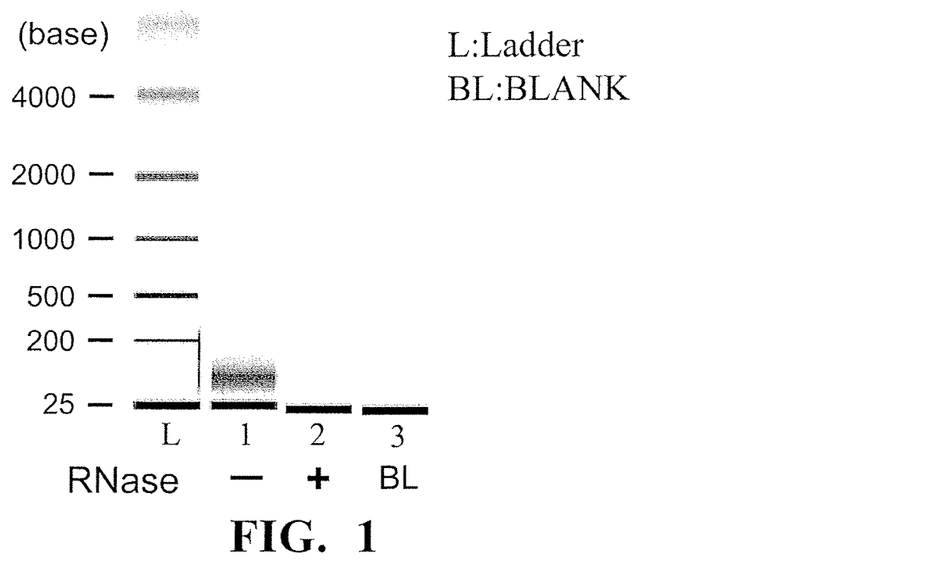
FIG. 1 shows electropherograms of nucleic acid extracted from serum in Example 1 using a solution according to an embodiment of the present invention.

After heat denaturation of 1 µL each of the RNA samples obtained in (3a) and (3b) at 70° C. for 2 minutes, each sample was rapidly cooled. The samples were then subjected to electrophoresis using "Agilent RNA 6000 pico kit" manufactured by Agilent Technologies Inc. (model number, 5067-1513). The results are shown in FIG. 1. Further, by the Smear Analysis function of "Bioanalyzer 2100", the peak area of 25 to 500 nt was calculated to confirm the peak size and the amount (concentration) of nucleic acid detected.

In the sample (3a) wherein enzyme treatment was not carried out, only a single peak having a size of less than 200 bases was found (lane 1). The amount of nucleic acid calculated in this case was 816 pg/µL. On the other hand, in the electrophoretic pattern of the RNase-treated sample (3b), no peak was detected (lane 2). The amount of nucleic acid calculated in this case was 61 pg/µL. In order to confirm the noise in the detection system, the same operation as in Example 1 was carried out using PBS containing no nucleic acid, instead of serum (lane 3, BLANK). Since the amount of nucleic acid calculated in this case was 63 pg/4, the amount of nucleic acid calculated for lane 2 was considered to be due to the noise. From the above results, the extracted nucleic acid could be confirmed to be RNA which does not contain DNA. Since RNA having 22 to 25 bases and the peak obtained in the present Example showed similar migration distances in electrophoresis, the RNA found in lane 1 was considered to have 22 to 25 bases.

The above results are summarized in Table 1.

Comparative Example 1

(1) Preparation of Solution for RNA Extraction

The solution described in Patent Document 2 was prepared with the same composition as in Example 1 except that the phenol concentration was 50% by volume in terms of the final concentration of the solution.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(3b) Purification and Concentration of RNA from Aqueous Layer—with RNase Treatment—

The operation was carried out in the same manner as in Example 1.

(3c) Purification and Concentration of RNA from Aqueous Layer—with DNase Treatment—

The operation was carried out in the same manner as in (3b) in Example 1 except that the aqueous layer containing RNA was treated with DNase instead of the RNase in (3b), to obtain a purified and concentrated sample. Other conditions were the same as in Example 1.

(4) Evaluation of Purity by Electrophoresis

Figure 2:
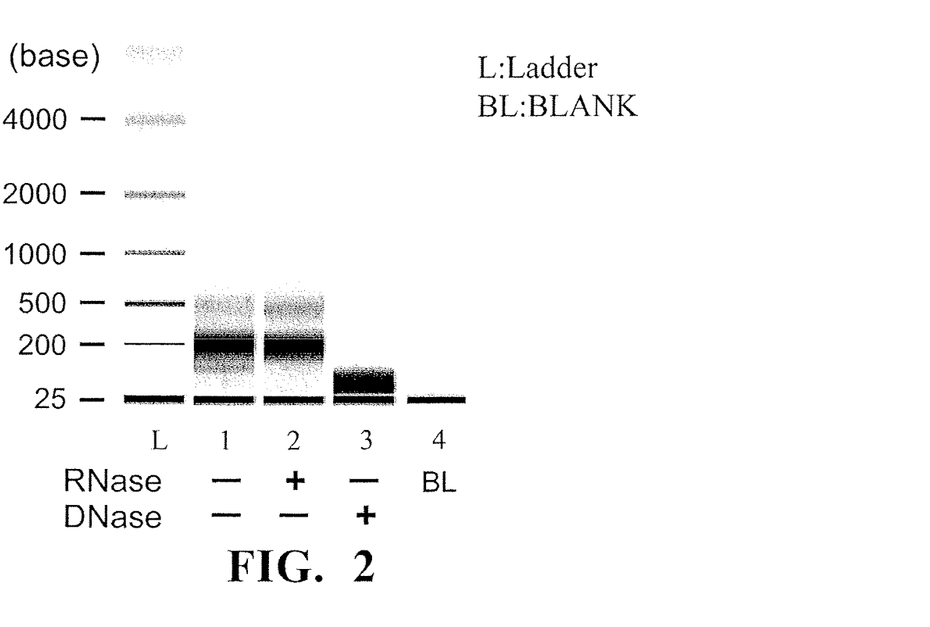
FIG. 2 shows electropherograms of nucleic acid extracted from serum in Comparative Example 1 using a solution described in Patent Document 2.

The operation was carried out in the same manner as in Example 1. The results are shown in FIG. 2.

In the sample wherein enzyme treatment was not carried out, two strong peaks (corresponding to numbers of bases of about 200 and about 500) and one weak peak (corresponding to the same number of bases as in Example 1) were detected (lane 1). In the sample treated with RNase, the peaks of 200 bases and 500 bases hardly changed, and it was therefore found that the two peaks were not due to RNA (lane 2). On the other hand, the single weak peak has disappeared, and this peak was therefore confirmed to be due to RNA as in the case of Example 1. In the DNase-treated sample, the two strong peaks have disappeared, and very short fragments due to degradation were detected (lane 3). Therefore, these two strong peaks were found to be due to contamination with DNA fragments.

Thus, when the solution containing 50% by volume of phenol was used, contamination with DNA was observed, and pure RNA could not be extracted.

The above results are summarized in Table 3.

Comparative Example 2

(1) Preparation of Solution for RNA Extraction

The same solution as the extraction solution described in Patent Document 1 was prepared except that the phenol concentration was 60% by volume. That is, the solution contained 60% by volume of phenol, 2M guanidinium thiocyanate, 0.1 M sodium acetate and 0.2% by volume of 2-mercaptoethanol in terms of the final concentrations, and the pH of the solution was 4.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(4) Evaluation of Purity by Electrophoresis

Figure 3:
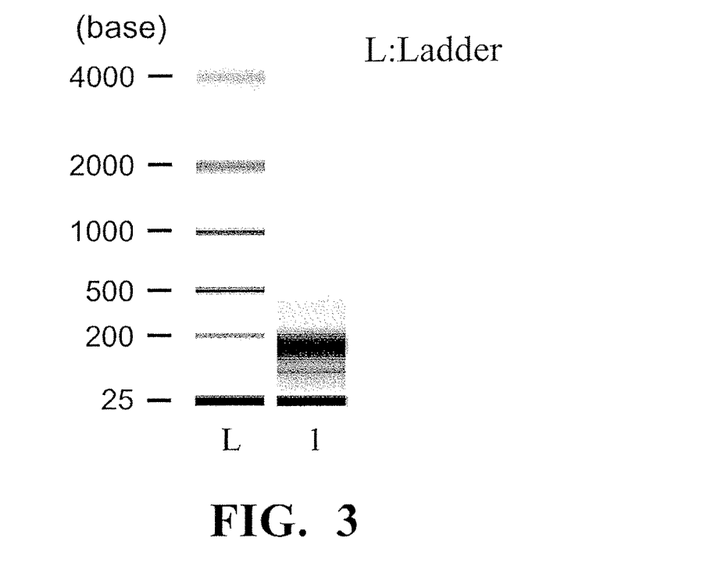
FIG. 3 shows an electropherogram of nucleic acid extracted from serum in Comparative Example 2 using a solution described in Patent Document 1.

The operation was carried out in the same manner as in Example 1. The result is shown in FIG. 3.

Three peaks similar to those in Comparative Example 1 were observed. Therefore, contamination with DNA fragments could be confirmed.

The above result is summarized in Table 3.

Example 2

(1) Preparation of Solution for RNA Extraction

A solution was prepared such that the composition of the solution is the same as in Example 1 except that the phenol concentration was 55% by volume in terms of the final concentration.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(3b) Purification and Concentration of RNA from Aqueous Layer—with RNase Treatment—

The operation was carried out in the same manner as in Example 1.

(4) Evaluation of Purity by Electrophoresis

Figure 4:
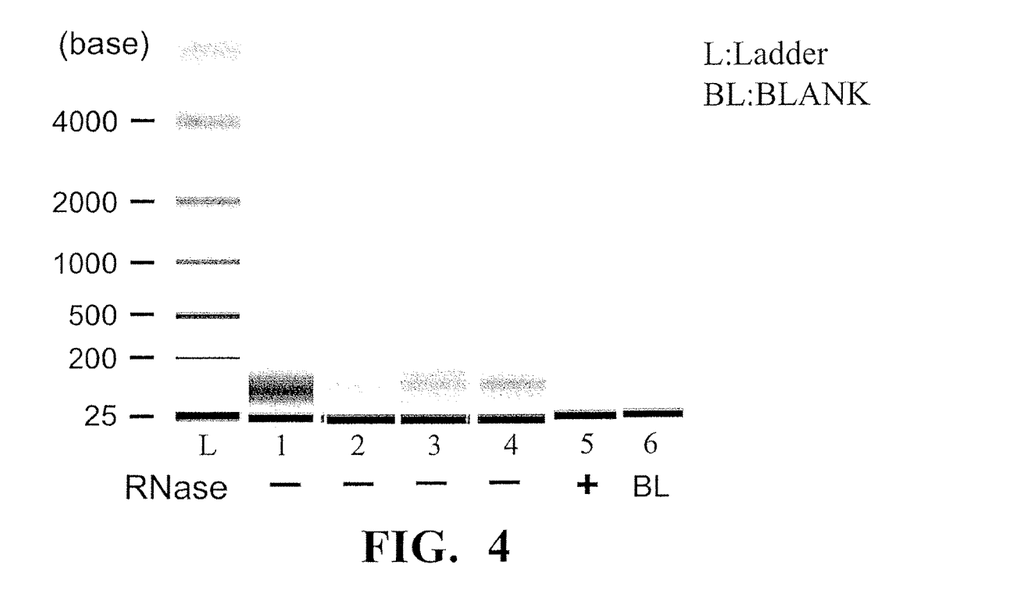
FIG. 4 shows electropherograms of nucleic acid extracted from serum in Examples 2 to 5 using solutions according to embodiments of the present invention.

The operation was carried out in the same manner as in Example 1. The results are shown in FIG. 4.

The same peak as in Example 1 was detected (lane 1), and it could be confirmed that only RNA was extracted with high purity. Since the peak in the RNase-treated sample (lane 5; RNase (+)) was as weak as that in BLANK, it could be confirmed that the extracted nucleic acid contained only RNA.

The above results are summarized in Table 1.

Example 3

(1) Preparation of Solution for RNA Extraction

A solution was prepared such that the composition of the solution is the same as in Example 1 except that the phenol concentration was 65% by volume in terms of the final concentration.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 2 in FIG. 4.

The same peak as in Example 1 was detected, and it could be confirmed that only RNA was extracted with high purity.

The above result is summarized in Table 1.

Example 4

(1) Preparation of Solution for RNA Extraction

A solution was prepared such that the composition of the solution is the same as in Example 1 except that the phenol concentration was 53% by volume in terms of the final concentration.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 3 in FIG. 4.

The same peak as in Example 1 was detected, and it could be confirmed that only RNA was extracted with high purity.

The above result is summarized in Table 1.

Example 5

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 240 μL of chloroform was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 4 in FIG. 4.

The same peak as in Example 1 was detected, and it could be confirmed that only RNA was extracted with high purity.

The above result is summarized in Table 1.

Example 6

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of 4-bromoveratrole was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 1 in FIG. 5.

Figure 5:
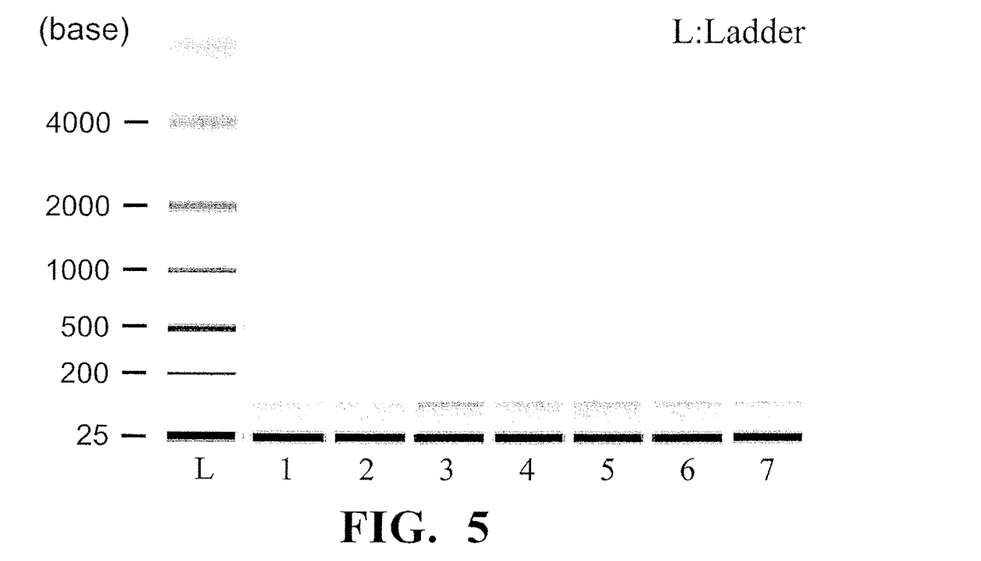
FIG. 5 shows electropherograms of nucleic acid extracted from serum in Examples 6 to 12 using solutions according to embodiments of the present invention.

The same peak as in Example 1 was detected, and it could be confirmed that only RNA was extracted with high purity.

The above result is summarized in Table 1.

Example 7

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of 6-bromo-1,4-benzodioxane was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 2 in FIG. 5.

The same peak as in Example 1 was detected, and it could be confirmed that only RNA was extracted with high purity.

The above result is summarized in Table 1.

Example 8

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of 1-bromo-4-trifluoromethoxybenzene was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 3 in FIG. 5.

The same peak as in Example 1 was detected, and it could be confirmed that only RNA was extracted with high purity.

The above result is summarized in Table 1.

Example 9

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of 1-bromo-2,4-dimethoxybenzene was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 4 in FIG. 5.

The same peak as in Example 1 was detected, and it could be confirmed that only RNA was extracted with high purity.

The above result is summarized in Table 1.

Example 10

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of 4-fluoroanisole was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was, carried out in the same manner as in Example 1. The result is shown in lane 5 in FIG. 5.

The same peak as in Example 1 was detected, and it could be confirmed that only RNA was extracted with high purity.

The above result is summarized in Table 2.

Example 11

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of 4-bromotoluene was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 6 in FIG. 5.

The same peak as in Example 1 was detected, and it could be confirmed that only RNA was extracted with high purity.

The above result is summarized in Table 2.

Example 12

(1) Preparation of Solution for RNA Extraction

The solution having the same composition as in Example 1 was prepared.

(2) RNA Extraction from Biological Sample

The operation was carried out in the same manner as in Example 1 using serum as the biological sample, except that 100 μL of ethyl 4-bromobutyrate was added instead of 60 μL of p-bromoanisole to the homogenate.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 7 in FIG. 5.

The same peak as in Example 1 was detected, and it could be confirmed that only RNA was extracted with high purity.

The above result is summarized in Table 2.

Example 13

(1) Preparation of Solution for RNA Extraction

A solution was prepared by adding hydrochloric acid to the solution prepared in Example 1 such that the pH of the solution was adjusted to 4.2.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 1 in FIG. 6.

Figure 6:
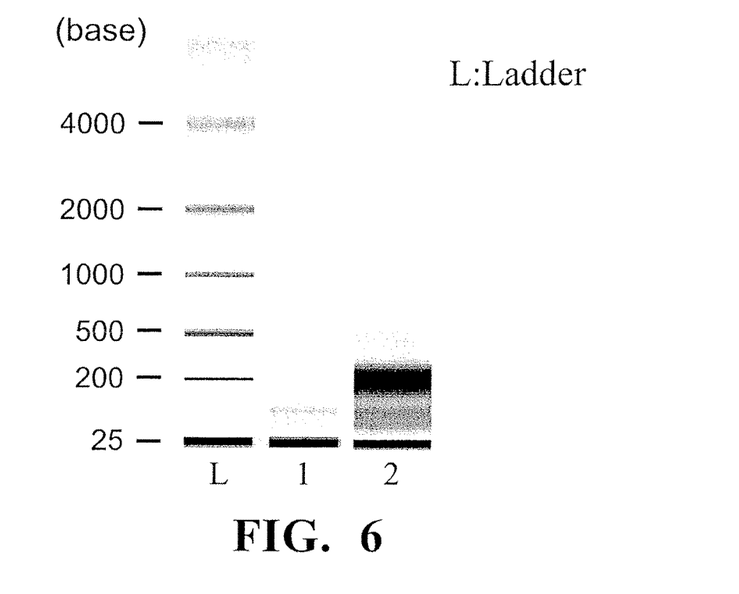
FIG. 6 shows electropherograms of nucleic acid extracted from serum in Example 13 and Comparative Example 3 using a solution according to an embodiment of the present invention and a solution described in Patent Document 3.

The same peak as in Example 1 was detected also in the case where the pH of the solution was 4.2, and it could be confirmed that only RNA was extracted with high purity.

The above result is summarized in Table 2.

Comparative Example 3

(1) Preparation of Solution for RNA Extraction

A solution was prepared by adding hydrochloric acid to the solution prepared in Comparative Example 1 such that the pH of the solution was adjusted to 3.6.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(4) Evaluation of Purity by Electrophoresis

The operation was carried out in the same manner as in Example 1. The result is shown in lane 2 in FIG. 6. The same three peaks as in Comparative Example 1 were observed. By this, it could be confirmed that, in cases where the solution containing 50% by volume of phenol is used, contamination with DNA fragments occurs also at a pH of 3.6.

The above result is summarized in Table 3.

Example 14

(1) Preparation of Solution for RNA Extraction

The solution having the same composition as in Example 1 was prepared.

(2) RNA Extraction from Biological Sample

The operation was carried out in the same manner as in Example 1 except that cultured cells (HEK293 cells) suspended in 300 μL of PBS were used as the biological sample, instead of 300 μL of serum.

(3a) Purification and Concentration of RNA from Aqueous Layer—without Enzyme Treatment—

The operation was carried out in the same manner as in Example 1 except that 1.25 volumes, instead of 1.5 volumes, of ethanol was added to the aqueous layer.

(3b) Purification and Concentration of RNA from Aqueous Layer—with RNase Treatment—

The operation was carried out in the same manner as in Example 1 except that 1.25 volumes, instead of 1.5 volumes, of ethanol was added to the aqueous layer.

(4) Evaluation of Purity by Electrophoresis

Figure 7:
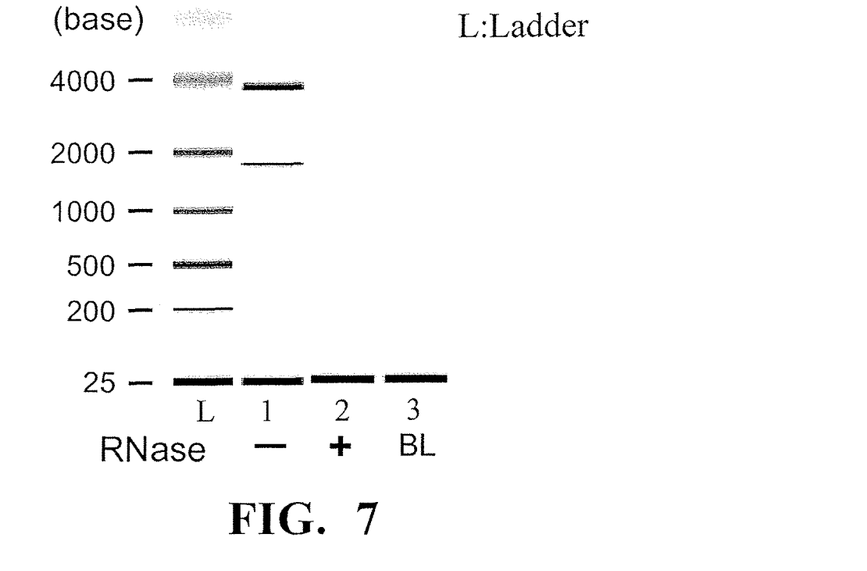
FIG. 7 shows electropherograms of nucleic acid extracted from cultured cells in Example 14 using a solution according to an embodiment of the present invention.

The operation was carried out in the same manner as in Example 1 except that "Agilent RNA 6000 nano kit" (model number, 5067-1511) (manufactured by Agilent Technologies Inc.) was used as the kit, instead of "Agilent RNA 6000 pico kit". The results are shown in FIG. 7.

It could be confirmed that, in the sample without enzyme treatment in (3a), 18S and 28S ribosome RNAs were extracted almost without degradation (RIN value: 2.3) (lane 1). The amount of nucleic acid calculated in this case was 79 ng/μL. In the result obtained with the RNase-treated sample in (3b), the same peak as in Example 1 was not detected at all (lane 2). The amount of nucleic acid calculated in this case was 4 ng/μL. The noise produced in the detection system when no sample was subjected to electrophoresis was investigated (lane 3) and, as a result, the amount of nucleic acid in this case was 2 ng/μL. Thus, the amount of nucleic acid in lane 2 was considered to be due to the noise. Based on these results, the extracted nucleic acid was confirmed to be entirely RNA.

The above results are summarized in Table 2.

Examples 15

(1) Preparation of Solution for RNA Extraction

The respective components of the solution were mixed such that their final concentrations were as described below, to prepare a solution for RNA extraction. That is, 60 μL of additional p-bromoanisole was added to 900 μL of the solution having the same composition as in Example 1, to prepare the solution.

58 vol % Phenol
5 vol % Glycerol
0.8 M Guanidinium thiocyanate (mixed as an aqueous solution)
0.4 M Ammonium thiocyanate (mixed as an aqueous solution)
0.1 M Sodium acetate buffer (mixed as an aqueous solution), adjusted to pH 5.
6.6 vol % p-Bromoanisole based on the total amount (100%) of the above components (2) RNA Extraction from Biological Sample By mixing 900 μL of the solution prepared in the above (1) and 300 μL of serum by vortexing, the sample was homogenized. The resulting homogenate was centrifuged at room temperature at 12,000×G for 10 minutes. By this, an aqueous layer containing RNA, and an organic layer and an intermediate layer containing DNA and proteins were formed. From these, 350 μL of the aqueous layer was separated into another tube.

(3a) Purification and Concentration of RNA from Aqueous Layer—without Enzyme Treatment—

The operation was carried out in the same manner as in Example 1.

(3b) Purification and Concentration of RNA from Aqueous Layer—with RNase Treatment—

The operation was carried out in the same manner as in Example 1.

(4) Evaluation of Purity by Electrophoresis

The operation was carried out in the same manner as in Example 1. The results are shown in lanes 1, 3 and 5 in FIG. 8.

Figure 8:
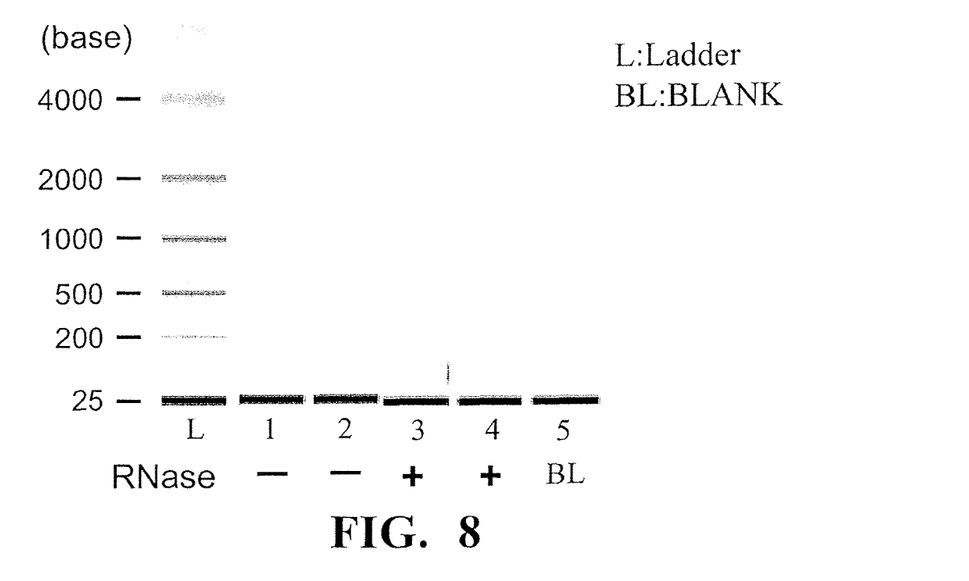
FIG. 8 shows electropherograms of nucleic acid extracted from serum in Examples 15 and 16 using solutions according to embodiments of the present invention.

The same peak as in Example 1 was detected, and it could be confirmed that only RNA was extracted with high purity (lane 1). Since the peak in the RNase-treated sample (lane 3; RNase (+)) was as weak as that in BLANK (lane 5), it could be confirmed that the extracted nucleic acid contained only RNA.

The above results are summarized in Table 2.

Examples 16

(1) Preparation of Solution for RNA Extraction

The respective components of the solution were mixed such that their final concentrations were as described below, to prepare a solution for RNA extraction. That is, 90 μL of additional chloroform was added to 900 μL of the solution having the same composition as in Example 1, to prepare the solution.

58 vol % Phenol
5 vol % Glycerol
0.8 M Guanidinium thiocyanate (mixed as an aqueous solution)
0.4 M Ammonium thiocyanate (mixed as an aqueous solution)
0.1 M Sodium acetate buffer (mixed as an aqueous solution), adjusted to pH 5.
10 vol % chloroform based on the total amount (100%) of the above components (2) RNA Extraction from Biological Sample By mixing 900 μL of the solution prepared in the above (1) and 300 μL of serum by vortexing, the sample was homogenized. The resulting homogenate was centrifuged at room temperature at 12,000×G for 10 minutes. By this, an aqueous layer containing RNA, and an organic layer and an intermediate layer containing DNA and proteins were formed. From these, 350 μL of the aqueous layer was separated into another tube.

(3a) Purification and Concentration of RNA from Aqueous Layer—without Enzyme Treatment—

The operation was carried out in the same manner as in Example 1.

(3b) Purification and Concentration of RNA from Aqueous Layer—with RNase Treatment—

The operation was carried out in the same manner as in Example 1.

(4) Evaluation of Purity by Electrophoresis

The operation was carried out in the same manner as in Example 1. The results are shown in lanes 2, 4 and 5 in FIG. 8.

The same peak as in Example 1 was detected, and it could be confirmed that only RNA was extracted with high purity (lane 2). Since the peak in the RNase-treated sample (lane 4;

RNase (+)) was as weak as that in BLANK (lane 5), it could be confirmed that the extracted nucleic acid contained only RNA.

The above results are summarized in Table 2.

Comparative Example 4

(1) Preparation of Solution for RNA Extraction

The solution having the same composition as in Comparative Example 3 was prepared except that the phenol concentration was 55% by volume.

(2) RNA Extraction from Biological Sample

The operation was carried out in the same manner as in Example 1 using serum as the biological sample.

(3a) Purification and Concentration of RNA from Aqueous Layer—Without Enzyme Treatment—

The operation was carried out in the same manner as in Example 1.

(3b) Purification and Concentration of RNA from Aqueous Layer—with RNase Treatment—

The operation was carried out in the same manner as in Example 1.

(4) Evaluation of Purity by Electrophoresis

Figure 9:
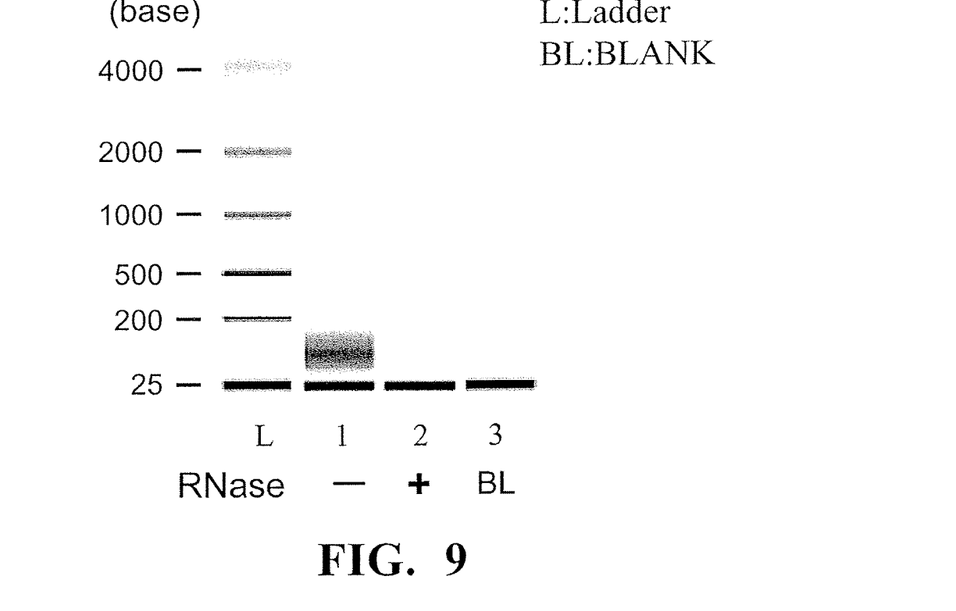
FIG. 9 shows electropherograms of nucleic acid extracted from serum in Comparative Example 4 using a solution described in Patent Document 3.

The operation was carried out in the same manner as in Example 1. The results are shown in FIG. 9.

In the sample without enzyme treatment in (3a), a rather broader peak compared to the peak in Example 1 was detected (lane 1), and the RNase-treated sample in (3b) also showed a peak (lane 2). Since the peak obtained with the RNase-treated sample (RNase(+)) was also broader than the peak in BLANK (lane 2), contamination with nucleic acid other than RNA (DNA) could be confirmed.

The above results are summarized in Table 3.

Example 17

(1) Preparation of Solution for RNA Extraction

The solution having the same composition as in Example 1 in terms of the final concentrations was prepared, except that the pH of was adjusted to 4.

(2) RNA Extraction from Biological Sample

The operation was carried out in the same manner as in Example 1 using serum as the biological sample.

(3a) Purification and Concentration of RNA from Aqueous Layer—without Enzyme Treatment—

The operation was carried out in the same manner as in Example 1.

(3b) Purification and Concentration of RNA from Aqueous Layer—with RNase Treatment—

The operation was carried out in the same manner as in Example 1.

(4) Evaluation of Purity by Electrophoresis

Figure 10:
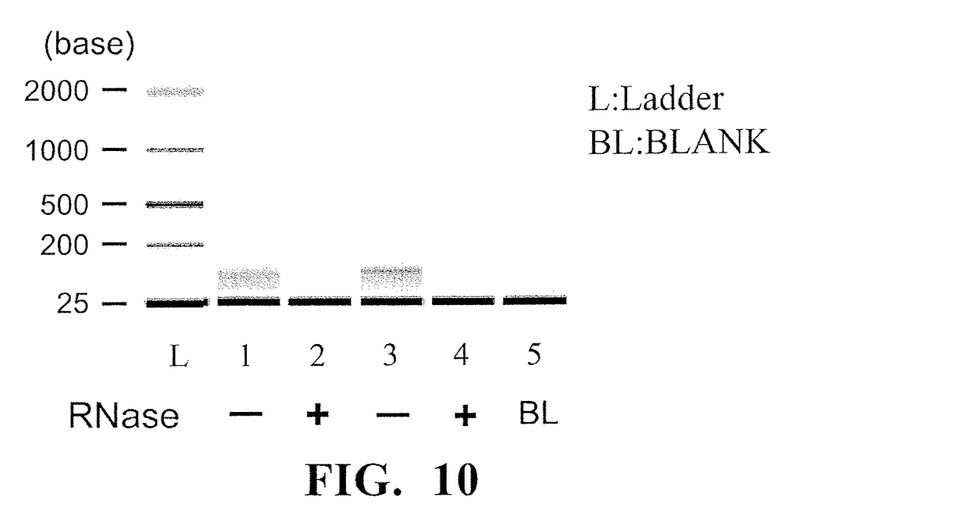
FIG. 10 shows electropherograms of nucleic acid extracted from serum in Examples 17 and 18 using solutions according to embodiments of the present invention.

The operation was carried out in the same manner as in Example 1. The results are shown in FIG. 10 (lanes 1, 2 and 5).

The same peak as in Example 1 was detected, and it could be confirmed that only RNA was extracted with high purity (lane 1). Since the peak in the RNase-treated sample (lane 2; RNase (+)) was as weak as that in BLANK (lane 5), it could be confirmed that the extracted nucleic acid contained only RNA.

The above results are summarized in Table 2.

Example 18

(1) Preparation of Solution for RNA Extraction

The solution having the same composition as in Example 1 in terms of the final concentrations was prepared, except that the pH was adjusted to 6.

(2) RNA Extraction from Biological Sample

The operation was carried out in the same manner as in Example 1 using serum as the biological sample.

(3a) Purification and Concentration of RNA from Aqueous Layer—Without Enzyme Treatment—

The operation was carried out in the same manner as in Example 1.

(3b) Purification and Concentration of RNA from Aqueous Layer—With RNase Treatment—

The operation was carried out in the same manner as in Example 1.

(4) Evaluation of Purity by Electrophoresis

The operation was carried out in the same manner as in Example 1. The results are shown in FIG. 10 (lanes 3, 4 and 5).

The same peak as in Example 1 was detected, and it could be confirmed that only RNA was extracted with high purity (lane 3). Since the peak in the RNase-treated sample (lane 4; RNase (+)) was as weak as that in BLANK (lane 5), it could be confirmed that the extracted nucleic acid contained only RNA.

The above results are summarized in Table 2.

TABLE 1

| | Example 1 | Example 2 | Example 3 | Example 4 | Example 5 | Example 6 | Example 7 | Example 8 | Example 9 |
|---|---|---|---|---|---|---|---|---|---|
| Composition of solution | | | | | | | | | |
| Phenol (% by volume) | 58 | 55 | 65 | 53 | 58 | 58 | 58 | 58 | 58 |
| Guanidinium thiocyanate (M) | 0.8 | 0.8 | 0.8 | 0.8 | 0.8 | 0.8 | 0.8 | 0.8 | 0.8 |
| Ammonium thiocyanate (M) | 0.4 | 0.4 | 0.4 | 0.4 | 0.4 | 0.4 | 0.4 | 0.4 | 0.4 |
| Glycerol (% by volume) | 5 | 5 | 5 | 5 | 5 | 5 | 5 | 5 | 5 |
| Sodium acetate (M) | 0.1 | 0.1 | 0.1 | 0.1 | 0.1 | 0.1 | 0.1 | 0.1 | 0.1 |
| 2-Mercaptoethanol (% by volume) | — | — | — | — | — | — | — | — | — |
| pH of solution | 5 | 5 | 5 | 5 | 5 | 5 | 5 | 5 | 5 |
| Organic solvent (added later) | Bromo-anisole | Bromo-anisole | Bromo-anisole | Bromo-anisole | Chloroform | Bromo-veratrole | Benzo-dioxane | Trifluoro-methoxy-benzene | Dimethoxy-benzene |
| Organic solvent (preliminarily contained) | — | — | — | — | — | — | — | — | — |
| Biological sample | Serum | Serum | Serum | Serum | Serum | Serum | Serum | Serum | Serum |

TABLE 1-continued

|  | Example 1 | Example 2 | Example 3 | Example 4 | Example 5 | Example 6 | Example 7 | Example 8 | Example 9 |
|---|---|---|---|---|---|---|---|---|---|
| Amount of nucleic acid extracted (pg/μL) | | | | | | | | | |
| Without enzyme treatment | 816 | 421 | | | | | | | |
| With RNase treatment | 61 | 37 | | | | | | | |
| With DNase treatment | — | — | | | | | | | |
| Blank | 63 | 41 | | | | | | | |
| Electropherogram | FIG. 1 | FIG. 4 | FIG. 4 | FIG. 4 | FIG. 4 | FIG. 5 | FIG. 5 | FIG. 5 | FIG. 5 |
| Figure number/lane number | Lane 1, 2 | Lane 1, 5 | Lane 2 | Lane 3 | Lane 4 | Lane 1 | Lane 2 | Lane 3 | Lane 4 |
| Purity of RNA extracted | good | good | good | good | good | good | good | good | good |

TABLE 2

|  | Example 10 | Example 11 | Example 12 | Example 13 | Example 14 | Example 15 | Example 16 | Example 17 | Example 18 |
|---|---|---|---|---|---|---|---|---|---|
| Composition of solution | | | | | | | | | |
| Phenol (% by volume) | 58 | 58 | 58 | 58 | 58 | 58 | 58 | 58 | 58 |
| Guanidinium thiocyanate (M) | 0.8 | 0.8 | 0.8 | 0.8 | 0.8 | 0.8 | 0.8 | 0.8 | 0.8 |
| Ammonium thiocyanate (M) | 0.4 | 0.4 | 0.4 | 0.4 | 0.4 | 0.4 | 0.4 | 0.4 | 0.4 |
| Glycerol (% by volume) | 5 | 5 | 5 | 5 | 5 | 5 | 5 | 5 | 5 |
| Sodium acetate (M) | 0.1 | 0.1 | 0.1 | 0.1 | 0.1 | 0.1 | 0.1 | 0.1 | 0.1 |
| 2-Mercaptoethanol (% by volume) | — | — | — | — | — | — | — | — | — |
| pH of solution | 5 | 5 | 5 | 4.2 | 5 | 5 | 5 | 4 | 6 |
| Organic solvent (added later) | Fluoro-anisole | Bromo-toluene | Ethyl Bromo-butyrate | Bromo-anisole | Bromo-anisole | — | — | Bromo-anisole | Bromo-anisole |
| Organic solvent (preliminarily contained) | — | — | — | — | — | Bromo-anisole | Chloro-form | — | — |
| Biological sample | Serum | Serum | Serum | Serum | Cultured cells | Serum | Serum | Serum | Serum |
| Amount of nucleic acid extracted (pg/μL) | | | | | | | | | |
| Without enzyme treatment | | | | | | 274 | 209 | 193 | 174 |
| With RNase treatment | | | | | | 24 | 29 | 25 | 22 |
| With DNase treatment | | | | | | — | — | — | — |
| Blank | | | | | | 41 | 41 | 38 | 38 |
| Electropherogram | FIG. 5 | FIG. 5 | FIG. 5 | FIG. 6 | FIG. 7 | FIG. 8 | FIG. 8 | FIG. 10 | FIG. 10 |
| Figure number/lane number | Lane 5 | Lane 6 | Lane 7 | Lane 1 | Lane 1, 2 | Lane 1, 3 | Lane 2, 4 | Lane 1, 2 | Lane 3, 4 |
| Purity of RNA extracted | good | good | good | good | good | good | good | good | good |

TABLE 3

|  | Comparative Example 1 | Comparative Example 2 | Comparative Example 3 | Comparative Example 4 |
|---|---|---|---|---|
| Composition of solution | | | | |
| Phenol (% by volume) | 50 | 60 | 50 | 55 |
| Guanidinium thiocyanate (M) | 0.8 | 2 | 0.8 | 0.8 |
| Ammonium thiocyanate (M) | 0.4 | — | 0.4 | 0.4 |
| Glycerol (% by volume) | 5 | — | 5 | 5 |
| Sodium acetate (M) | 0.1 | 0.1 | 0.1 | 0.1 |
| 2-Mercaptoethanol (% by volume) | — | 0.2 | — | — |
| pH of solution | 5 | 4 | 3.6 | 3.6 |
| Organic solvent (added later) | Bromoanisole | Bromoanisole | Bromoanisole | Bromoanisole |
| Organic solvent (preliminarily contained) | — | — | — | — |
| Biological sample | Serum | Serum | Serum | Serum |

TABLE 3-continued

|  | Comparative Example 1 | Comparative Example 2 | Comparative Example 3 | Comparative Example 4 |
|---|---|---|---|---|
| Amount of nucleic acid extracted (pg/μL) | | | | |
| Without enzyme treatment | 4796 | | | 302 |
| With RNase treatment | 784 | | | 78 |
| With DNase treatment | 499 | | | — |
| Blank | 42 | | | 54 |
| Electropherogram | FIG. 2 | FIG. 3 | FIG. 6 | FIG. 9 |
| Figure number/lane number | Lane 1-3 | Lane 1 | Lane 2 | Lane 1, 2 |
| Purity of RNA extracted | not good | not good | not good | not good |

What is claimed is:

1. A method for extracting RNA from a biological sample containing RNA and at least DNA, said method comprising the steps of:
homogenizing said biological sample together with a solution comprising:
(a) phenol in an amount of not less than 53% by volume based on the total amount of said solution, wherein the amount of phenol does not exceed a percentage that excludes any of components (b)-(e),
(b) an aliphatic alcohol having a plurality of hydroxyl groups in an amount of 3 to 10% by volume based on the total amount of said solution;
(c) a guanidinium salt at a concentration of 0.5 to 2.0 M based on the total amount of said solution;
(d) a thiocyanate at a concentration of 0.1 to 0.5 M based on the total amount of said solution; and
(e) a buffer for maintaining the pH of said solution at 4 to 6;
mixing the obtained homogenate with an organic solvent for separation of an aqueous layer;
centrifuging the obtained mixture; and
recovering an RNA-containing aqueous layer produced by the centrifugation.

2. The method according to claim 1, wherein said biological sample is a culture liquid of cultured cells.

3. The method according to claim 1, wherein said biological sample is a body fluid component of an organism.

4. The method according to claim 1, wherein said biological sample is a blood component of an organism.

5. The method according to claim 1, wherein subjecting the recovered RNA-containing aqueous layer, without a DNase treatment, to qRT-PCR, produces an amplification product that is not statistically different from an amplification product of the recovered RNA-containing aqueous layer which is subjected to a DNase treatment prior to qRT-PCR.

6. A method for extracting RNA from a biological sample containing RNA and at least DNA, said method comprising the steps of:
homogenizing said biological sample together with a solution comprising:
(a) phenol in an amount of not less than 53% by volume based on the total amount of said solution, wherein the amount of phenol does not exceed a percentage that excludes any of components (b)-(e);
(b) an aliphatic alcohol having a plurality of hydroxyl groups in an amount of 3 to 10% by volume based on the total amount of said solution;
(c) a guanidinium salt at a concentration of 0.5 to 2.0 M based on the total amount of said solution;
(d) a thiocyanate at a concentration of 0.1 to 0.5 M based on the total amount of said solution;
(e) a buffer for maintaining the pH of said solution at 4 to 6; and
(f) an organic solvent for separation of an aqueous layer, wherein the organic solvent is in addition to the phenol;
centrifuging the obtained homogenate; and
recovering an RNA-containing aqueous layer produced by the centrifugation.

7. The method according to claim 6, wherein said biological sample is a culture liquid of cultured cells.

8. The method according to claim 6, wherein said biological sample is a body fluid component of an organism.

9. The method according to claim 6, wherein said biological sample is a blood component of an organism.

* * * * *